United States Patent
Zhang et al.

(10) Patent No.: US 12,337,197 B1
(45) Date of Patent: Jun. 24, 2025

(54) AUTOMATIC POSITIONING DEVICE FOR HELICAL TOMOTHERAPY PLAN VERIFICATION

(71) Applicant: Guangzhou Institute of Cancer Research, the Affiliated Cancer Hospital, Guangzhou Medical University, Guangzhou (CN)

(72) Inventors: Guoqian Zhang, Guangzhou (CN); Xin He, Guangzhou (CN); Shuxu Zhang, Guangzhou (CN); Linjing Wang, Guangzhou (CN); Shuyu Wu, Guangzhou (CN); Yuliang Liao, Guangzhou (CN); Lu Zhou, Guangzhou (CN); Huijun Li, Guangzhou (CN); Lu Yang, Guangzhou (CN); Ruihao Wang, Guangzhou (CN); Liangqian Gou, Guangzhou (CN)

(73) Assignee: Guangzhou Institute of Cancer Research, the Affiliated Cancer Hospital, Guangzhou Medical University, Guangzhou (CN)

( * ) Notice: Subject to any disclaimer, the term of this patent is extended or adjusted under 35 U.S.C. 154(b) by 0 days.

(21) Appl. No.: 19/094,861

(22) Filed: Mar. 29, 2025

Related U.S. Application Data

(63) Continuation of application No. PCT/CN2024/112699, filed on Aug. 16, 2024.

(30) Foreign Application Priority Data

Jul. 5, 2024 (CN) .......................... 202410900036.9

(51) Int. Cl.
*A61N 5/10* (2006.01)

(52) U.S. Cl.
CPC ......... *A61N 5/1049* (2013.01); *A61N 5/1031* (2013.01); *A61N 2005/105* (2013.01); *A61N 2005/1076* (2013.01)

(58) Field of Classification Search
None
See application file for complete search history.

(56) References Cited

U.S. PATENT DOCUMENTS 10,702,715 B2 * 7/2020 Pearce .................. A61N 5/107
11,369,806 B2 * 6/2022 Laurence, Jr. ....... A61N 5/1081
(Continued)

FOREIGN PATENT DOCUMENTS

CN 104192757 A 12/2014
CN 104888355 A 9/2015
(Continued)

OTHER PUBLICATIONS

Retrieval report—First search dated Nov. 4, 2024 in SIPO application No. 202410900036.9.
(Continued)

*Primary Examiner* — Hoon K Song
(74) *Attorney, Agent, or Firm* — Pilloff Passino & Cosenza LLP; Rachel Pilloff; Sean Passino

(57) ABSTRACT

An automatic positioning device for helical tomotherapy plan verification is provided. The device includes a base located on a treatment bed of helical tomotherapy equipment, a lifting platform fixedly connected to a top of the base, a three-dimensional verification phantom fixedly connected to other ends of the two support rods, and an early warning component. A bearing platform is fixedly connected to a top of the lifting platform, a moving platform is arranged on the bearing platform, and ends of two support rods are fixedly connected to a side, close to the treatment bed, of the moving platform. The three-dimensional verification phan-
(Continued)

tom extends into a treatment aperture through the moving platform. The early warning component includes two early warning pieces respectively arranged on the two support rods.

7 Claims, 2 Drawing Sheets

(56) References Cited

U.S. PATENT DOCUMENTS

| | | | | |
|---|---|---|---|---|
| 2018/0133518 | A1* | 5/2018 | Harper | A61N 5/1049 |
| 2021/0069527 | A1* | 3/2021 | Peltola | A61N 5/1031 |

FOREIGN PATENT DOCUMENTS

| | | |
|---|---|---|
| CN | 109481856 A | 3/2019 |
| CN | 209728182 U | 12/2019 |
| CN | 115531739 A | 12/2022 |
| CN | 115869553 A | 3/2023 |
| CN | 117379705 A | 1/2024 |
| CN | 117959626 A | 5/2024 |
| EP | 4186562 A | 5/2023 |
| GB | 2531730 A | 5/2016 |

OTHER PUBLICATIONS

Notice of first Office action dated Nov. 5, 2024 in SIPO application No. 202410900036.9.
Retrieval report—Supplementary search dated Jan. 8, 2025 in SIPO application No. 202410900036.9.
Notification to Grant Patent Right for Invention dated Jan. 13, 2025 in SIPO application No. 202410900036.9.
International Search Report issued in corresponding PCT Application No. PCT/CN2024/112699 dated Dec. 23, 2024.
Zhang Fuli, Dose verification of intensity modulated spiral tomography radiotherapy plan by using two kinds of three-dimensional detector arrays, Chinese Journal of Medical Physics, Mar. 25, 2015, vol. 32, No. 2, pp. 218-220, 238 (abstract translated) doi: 10.3969/j.issn.1005-202X.2015.02.015 Full text.

* cited by examiner

AUTOMATIC POSITIONING DEVICE FOR HELICAL TOMOTHERAPY PLAN VERIFICATION

CROSS-REFERENCE TO RELATED APPLICATIONS

This application is a continuation of PCT/CN2024/112699, filed Aug. 16, 2024 and claims priority of Chinese Patent Application No. 202410900036.9, filed on Jul. 5, 2024, the entire contents of which are incorporated herein by reference.

TECHNICAL FIELD

The present disclosure relates to the field of medical device technology, and particularly to an automatic positioning device for helical tomotherapy plan verification.

BACKGROUND

Helical tomotherapy system (TOMO Therapy), which integrates intensity-modulated radiation therapy (IMRT), image-guided radiation therapy (IGRT), and dose-guided radiation therapy (DGRT), is the world's leading-edge tumor radiation therapy equipment. The innovative design of TOMO Therapy uses a helical computed tomography (CT) rotary scanning method combined with computer tomography image navigation and calibration, breaking through many limitations of traditional accelerators. Under CT guidance, 360-degree focused tomography irradiation of tumors is performed, providing efficient, precise, and safe treatment for malignant tumor patients. Before implementing helical tomotherapy, dose validation is required for individualized patient radiotherapy plans, using three-dimensional dose validation tools to measure the patient's plan and ensure that the designed radiotherapy plan is consistent with the actual irradiation dose, thereby ensuring the safety and accuracy of irradiation. Currently, ArcCheck or Delta4 three-dimensional dose three-dimensional verification phantoms are mainly used in clinical practice to validate helical tomotherapy plans.

However, the following issues exist in practice. Firstly, during the conventional IMRT or VMAT intensity-modulated plan validation, the position of the three-dimensional dose three-dimensional verification phantom is fixed. For the treatment plan validation of multiple patients, only one positioning is required, which is to align the center line marked on the surface of the cylindrical three-dimensional dose three-dimensional verification phantom with the field center. The field center is the center of the laser light, because the conventional linear accelerator has only one set of laser light system, and its isocenter position is fixed. The helical tomotherapy equipment has two sets of laser lights, namely the red laser light and the green laser light. The green laser light is fixed in position, representing the virtual field center, while the position of the red laser light may be moved for radiotherapy plans of different patients. During the helical tomotherapy plan verification, the center position of the red laser light (that is, the position of positioning for the three-dimensional verification phantom corresponding to each patient) is different, which means that for each radiotherapy plan verification, the physicist needs to enter the computer room and reposition the three-dimensional verification phantom according to the position of the red laser light corresponding to the radiotherapy plan of the patient, that is, move the treatment bed in up-and-down, left-and-right and forward-and-backward directions respectively. This process is time-consuming, the plan verification efficiency is low, and the pass rate of plan verification is affected when the positioning accuracy is not enough.

Secondly, in the previous dose verification of helical tomotherapy plan, the treatment bed was the direct carrier of three-dimensional verification phantom. It is necessary to move the position of the red laser light to find a suitable positioning center to effectively measure the prescription dose area of the actual treatment plan when generating the verification plan of the patient by using the three-dimensional dose three-dimensional verification phantom. However, when the tumor position is eccentrically distributed, the positioning center of the three-dimensional dose three-dimensional verification phantom will deviate in the X coordinate direction, that is, the left and right direction. When the deviation exceeds a certain range, due to the limitation of the aperture size, the left and right movement range of the treatment bed is limited (only 2.5 centimeters (cm)), which will cause the positioning position of the three-dimensional verification phantom to be biased towards one side of the treatment bed during the plan verification of eccentric tumors. At this time, the phantom is at risk of falling, and the phantom may not be positioned smoothly in serious cases, and the prescription dose area of the actual treatment plan may not be effectively measured.

Thirdly, compared to conventional linear accelerators, TOMO has significant advantages in treating multiple lesions or "longer" tumors throughout the body, such as radiotherapy of the whole central nervous system. However, there is often such a problem in the verification of long tumor radiotherapy plans: the effective measurement length of the three-dimensional dose three-dimensional verification phantom is only 20-30 cm, and high-energy rays often irradiate the circuit board part of the verification equipment, resulting in the circuit board being unable to work properly. In mild cases, the dose measurement would be inaccurate, and in severe cases, it would cause the verification equipment to malfunction, resulting in economic losses.

SUMMARY

An objective of the present disclosure is to provide an automatic positioning device for helical tomotherapy plan verification to address the aforementioned issues in the prior art.

In order to achieve the above objectives, the present disclosure provides the following solution: an automatic positioning device for helical tomotherapy plan verification, including:

a base located on a treatment bed of helical tomotherapy equipment;

a lifting platform fixedly connected to a top of the base, where a bearing platform is fixedly connected to a top of the lifting platform, a moving platform is arranged on the bearing platform, and ends of two support rods are fixedly connected to a side, close to the treatment bed, of the moving platform;

a three-dimensional verification phantom fixedly connected to other ends of the two support rods, where the three-dimensional verification phantom extends into a treatment aperture through the moving platform; and an early warning component including two early warning pieces, where the two early warning pieces are respectively arranged on the two support rods, and the early warning pieces are aligned with a circuit of the three-dimensional verification phantom to monitor a radiation dose received by the circuit of the three-dimensional verification phantom.

In some embodiments, each of the early warning pieces includes a sleeve, and the sleeve is sleeved on each of the support rods and is slidably connected to each of the support rods, and an ionization chamber is arranged in the sleeve, and the ionization chamber is configured for monitoring an irradiation threshold of rays.

In some embodiments, the lifting platform is a scissor lifting platform, and multiple metal sleeves are arranged outside the lifting platform, and the multiple metal sleeves are sleeved layer by layer.

In some embodiments, the moving platform is a biaxial moving platform.

In some embodiments, the sleeve is an equivalent water material sleeve.

In some embodiments, a counterweight is fixedly connected to an end, away from the treatment aperture, of the bearing platform.

In some embodiments, each of four corners of a bottom of the base is provided with a through hole, and a support nut is threadedly connected in the through hole.

In some embodiments, the sleeve is threadedly connected to positioning bolts, and ends of the positioning bolts penetrate through the sleeve to contact with the support rod.

Compared to the prior art, the present disclosure has the following advantages and technical effects.

According to the automatic positioning device for helical tomotherapy plan verification provided by the present disclosure, the position of the base may be adjusted on the treatment bed, and the combination of the lifting platform and the moving platform enables the three-axis movement of the three-dimensional verification phantom, thereby achieving the position adjustment of the phantom and ensuring effective measurement of the prescription dose area of the actual treatment plan. When the circuit of the three-dimensional verification phantom comes into contact with high-energy rays, the alarm is triggered by the set early warning component, ensuring the normal operation of the circuit board and thus ensuring accurate measurement. The device is simple in structure and convenient in adjustment, ensuring the effective measurement of the prescription dose area of the actual treatment plan and the measurement accuracy.

BRIEF DESCRIPTION OF THE DRAWINGS

In order to explain the embodiments of the present disclosure or the technical solution in the prior art more clearly, the drawings needed in the embodiments will be briefly introduced below. Apparently, the drawings in the following description are only some embodiments of the present disclosure. For one of ordinary skill in the art, other drawings may be obtained according to these drawings without creative effort.

DETAILED DESCRIPTION OF THE EMBODIMENTS

In the following, the technical solutions in the embodiments of the present disclosure will be clearly and completely described with reference to the attached drawings. Apparently, the described embodiments are only a part of the embodiments of the present disclosure, but not all the embodiments. Based on the embodiments in the present disclosure, all other embodiments obtained by one of ordinary skill in the art without creative effort belong to the protection scope of the present disclosure.

In order to make the above objects, features and advantages of the present disclosure more obvious and easier to understand, the present disclosure will be further described in detail with the attached drawings and specific embodiments.

Figure 1:
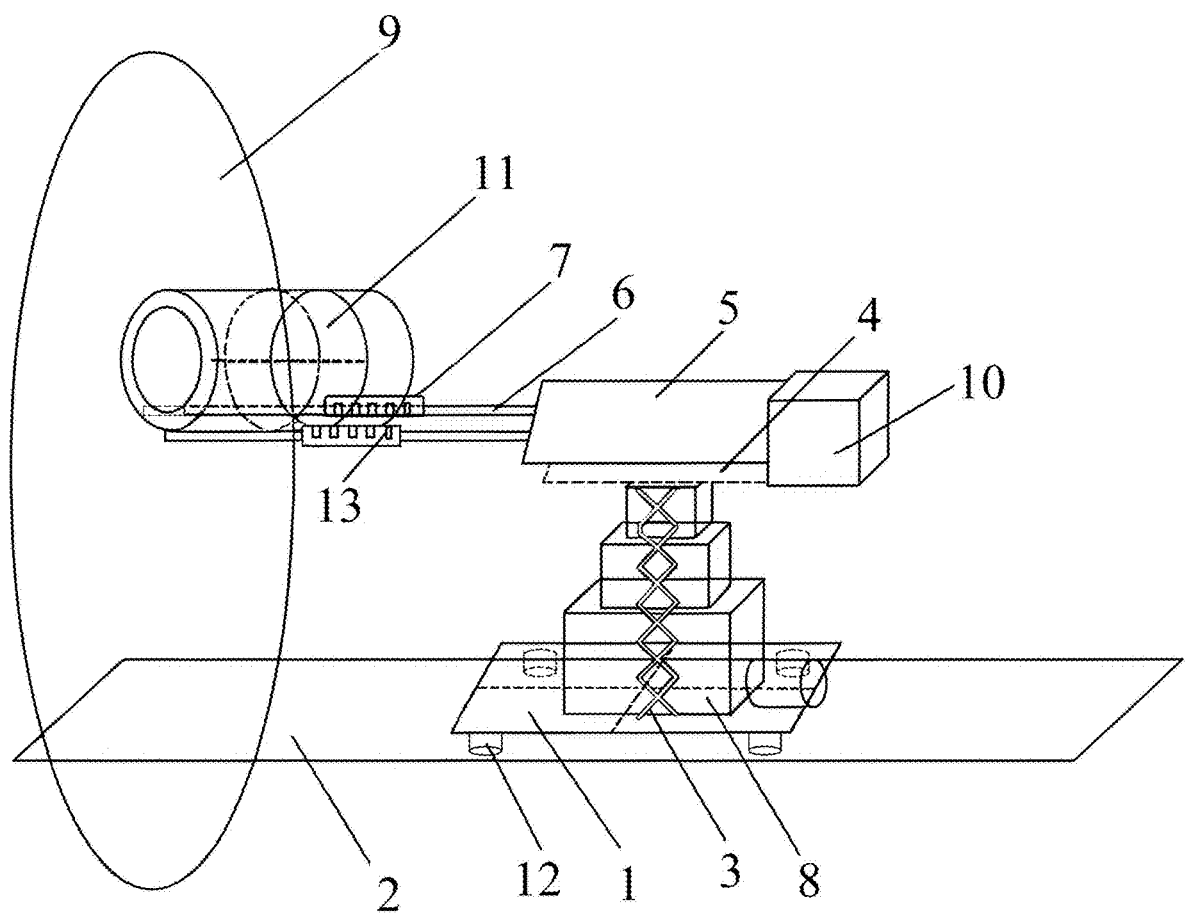
FIG. 1 is a schematic diagram of an overall structure according to the present disclosure.
Figure 2:
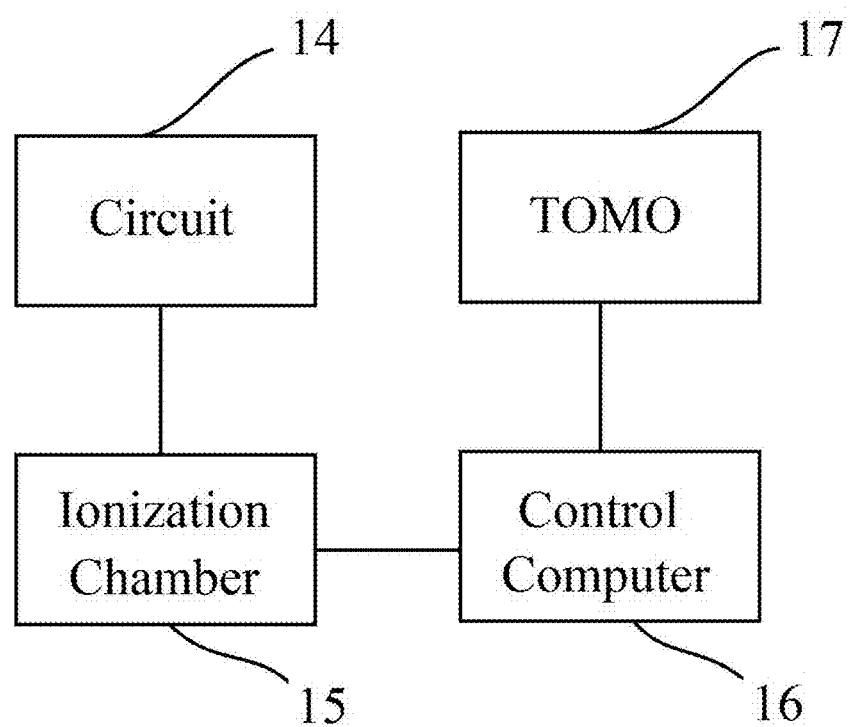
FIG. 2 is a block diagram of a control system according to the present disclosure.

With reference to FIGS. 1 and 2, the present disclosure provides an automatic positioning device for helical tomotherapy plan verification, which includes a base 1, a lifting platform 3, a three-dimensional verification phantom 11 and an early warning component.

The base 1 is located on the treatment bed 2 of the helical tomotherapy equipment.

The lifting platform 3 is fixedly connected to the top of the base 1, a bearing platform 4 is fixedly connected to the top of the lifting platform 3, a moving platform 5 is arranged on the bearing platform 4, and ends of two support rods 6 are fixedly connected to the side of the moving platform 5 close to the treatment bed 2.

The three-dimensional verification phantom 11 is fixedly connected to the other ends of the two support rods 6, the three-dimensional verification phantom 11 extends into a treatment aperture 9 through the moving platform 5.

The early warning component includes two early warning pieces, the two early warning pieces are respectively arranged on the two support rods 6, and the early warning pieces are aligned with the circuit 14 of the three-dimensional verification phantom 11 for monitoring the circuit of the three-dimensional verification phantom 11.

In one embodiment of the present disclosure, the device is used in the following scenario: the treatment bed 2 serves as the carrier of the device, and their relative positions remain unchanged. The device serves as the carrier of the three-dimensional verification phantom 11. For different patients, the three-dimensional verification phantom 11 moves to different positions based on the radiotherapy plan settings. It should be noted that during the positioning stage, the three-dimensional verification phantom 11 will not enter the treatment aperture 9 of radiotherapy equipment, but during the radiation emission of radiotherapy equipment, that is, during the plan verification, the treatment bed 2 will enter the treatment aperture 9, and then the device and the three-dimensional verification phantom 11 would also enter the treatment aperture 9 for dose measurement. During the implementation of the plan verification, that is, during the beam emission of the radiotherapy equipment, the relative positions of the treatment bed 2, the device and the three-dimensional verification phantom 11 would remain unchanged.

In an embodiment, the early warning piece includes a sleeve 7, and the sleeve 7 is sleeved on the support rod 6 and is slidably connected to the support rod 6, and an ionization chamber 15 is arranged in the sleeve 7, and the ionization chamber is used for monitoring irradiation threshold of rays.

In one embodiment of the present disclosure, the sleeve 7 contains an ionization chamber capable of monitoring high-energy rays inside. The ionization chamber is irradiated by high-energy rays, and dose information may be sent to the control computer 16. The position of the sleeve 7 may be adjusted in cross-section, that is, in the direction of bed forward and withdraw, and may be aligned with the circuit of the three-dimensional verification phantom 11, so as to monitor whether high-energy rays irradiate the ionization chamber and the circuit part of the three-dimensional verification phantom 11. When the high-energy rays irradiate the circuit part, that is, the ionization chamber part is irradiated by rays, and the ionization chamber monitors that the radiation irradiation reaches a threshold, the control computer may issue an alarm. When the cumulative dose of subsequent monitoring reaches the second threshold, the three-dimensional verification phantom 11 may be automatically controlled to move out.

In an embodiment, the lifting platform 3 is a scissor lifting platform, and multiple metal sleeves 8 are arranged outside the lifting platform 3, and the multiple metal sleeves 8 are sleeved layer by layer.

In one embodiment of the present disclosure, the lifting platform is a scissor lifting platform, and multiple metal sleeves 8 are sleeved outside, thereby achieving sheathing.

In an embodiment, the moving platform 5 is a biaxial moving platform.

In one embodiment of the present disclosure, the moving platform 5 is a biaxial moving platform, that is, an X-axis and Y-axis moving platform. The moving platform is driven to move horizontally and vertically by arranging lead screws, thereby driving the three-dimensional verification phantom 11 to move horizontally and vertically, and the three-dimensional verification phantom 11 may move in the X-axis, Y-axis and Z-axis directions in cooperation with the lifting platform 3.

In an embodiment, the sleeve 7 is an equivalent water material sleeve.

In an embodiment, a counterweight 10 is fixedly connected to the end of the bearing platform 4 away from the treatment aperture 9.

The counterweight 10 is located at the tail end of the overall structure to ensure the balance of the overall structure.

In an embodiment, each of the four corners of the bottom of the base 1 is provided with a through hole, and a support nut 12 is threadedly connected in the through hole.

The support nut 12 is rotatable, thereby enabling the four corners of the base 1 to be raised or lowered in height, and the base 1 may be horizontally adjusted by rotating the support nut 12.

In an embodiment, the sleeve 7 is threadedly connected to positioning bolts 13, and ends of the positioning bolts penetrate through the sleeve 7 to contact with the support rods 6.

The set positioning bolts are screwed to contact the support rods 6, the position of the sleeve 7 is limited to ensure its stability during the alignment with the circuit of the three-dimensional verification phantom 11.

The present disclosure provides the automatic positioning device for helical tomotherapy plan verification. When in use, firstly, the three-dimensional verification phantom 11 is fixed on the support rods 6, and the sleeves 7 are moved to keep the positions of the ionization chambers consistent with the circuit board part of the three-dimensional verification phantom 11 in cross-section. The red laser light of the TOMO equipment is moved to a certain position with the spatial coordinates of X', Y', Z', and the positioning is carried out based on the red laser according to the scale line on the base 1 of the device. This position serves as the initial isocenter position of the three-dimensional verification phantom 11 with the spatial coordinates of 0, 0, 0. At this time, the positioning mark line of the three-dimensional verification phantom 11 is aligned with the green laser, and the spatial coordinates are 0, 0, 0, and the central coordinates of the moving platform 5 are $X_0, Y_0, Z_0$. So far, the relative spatial positions of the three-dimensional verification phantom 11, the base 1 of the device, the moving platform 5 and the virtual field center of the TOMO 17 have all been determined.

After positioning, the verification plan of a certain patient is started. Firstly, the verification plan data, especially the coordinate data of the red laser light, is transmitted to the control computer. The control computer sets the coordinate data of the red laser light as $X_1, Y_1, Z_1$, that is, the target coordinate data of the three-dimensional verification phantom 11 is converted into the left-and-right movement data $X_1'$ and forward-and-backward movement data $Y_1'$ of the moving platform 5, and the height data $Z_1'$ of the lifting platform 3. Then, the moving platform 5 and the lifting platform 3 are controlled to reach the predetermined target position $X_1', Y_1', Z_1'$. At this time, the positioning mark line of the three-dimensional verification phantom 11 corresponds to the corresponding position $X_1, Y_1, Z_1$ of the red laser light, so that the positioning of the three-dimensional verification phantom 11 of the patient verification plan is automatically completed. With the implementation of the verification plan, the treatment bed continuously moves forward. When the high-energy rays irradiate the circuit part, that is, the ionization chamber part is irradiated by the ray, and the ionization chamber monitors that the ray irradiation reaches the threshold, the control computer immediately issues an early warning to remind the physicist. If the beam emission of the rays does not stop, and the cumulative dose monitored by the ionization chamber reaches the second threshold, the moving platform 5 is automatically driven to move in the direction of bed withdrawal and exit the treatment aperture of the TOMO to automatically avoid further irradiation and prevent potential circuit damage.

When using this device as the carrier of the TOMO radiotherapy three-dimensional dose three-dimensional verification phantom 11 for dose verification, the three-dimensional dose three-dimensional verification phantom has a larger measurement range in the left-and-right direction, providing advantages for the verification of eccentric tumor radiotherapy plans.

In the description of the present disclosure, it should be understood that the terms "longitudinal", "transverse", "up", "down", "front", "back", "left", "right", "vertical", "horizontal", "top", "bottom", "inside", "outside", etc. indicate orientation or positional relationships based on the orientation or positional relationships shown in the accompanying drawings, only for the convenience of describing the present disclosure, and do not indicate or imply that the device or element referred to must have a specific orientation, be constructed and operated in a specific orientation, and therefore cannot be understood as a limitation of the present disclosure.

The above-mentioned embodiments only describe the preferred mode of the present disclosure, and do not limit the scope of the present disclosure. Under the premise of not departing from the design spirit of the present disclosure, various modifications and improvements made by one of ordinary skill in the art to the technical solution of the present disclosure should fall within the protection scope of the present disclosure.

What is claimed is:

1. An automatic positioning device for helical tomotherapy plan verification, comprising:
   a base located on a treatment bed of helical tomotherapy equipment;
   a lifting platform fixedly connected to a top of the base, wherein a bearing platform is fixedly connected to a top of the lifting platform, a moving platform is arranged on the bearing platform, and ends of two support rods are fixedly connected to a side, close to the treatment bed, of the moving platform;

a three-dimensional verification phantom fixedly connected to other ends of the two support rods, wherein the three-dimensional verification phantom extends into a treatment aperture through the moving platform; and an early warning component comprising two early warning pieces, wherein the two early warning pieces are respectively arranged on the two support rods, and the early warning pieces are aligned with a circuit of the three-dimensional verification phantom to monitor a radiation dose received by the circuit of the three-dimensional verification phantom;

wherein each of the early warning pieces comprises a sleeve, and the sleeve is sleeved on each of the support rods and is slidably connected to each of the support rods, and an ionization chamber is arranged in the sleeve, and the ionization chamber is configured for monitoring an irradiation threshold of rays;

when in use, a position of the ionization chamber is enabled to be consistent with a circuit board part of the three-dimensional verification phantom in cross-section, a red laser light of TOMO equipment is moved to a certain position with spatial coordinates of X', Y', Z', and positioning is carried out based on a red laser according to a scale line on the base of the device; spatial coordinates of an initial isocenter position of the three-dimensional verification phantom are 0, 0, 0; at this time, a positioning mark line of the three-dimensional verification phantom is aligned with a green laser with spatial coordinates of 0, 0, 0, and central coordinates of the moving platform are $X_0$, $Y_0$, $Z_0$;

coordinate data of the red laser light is transmitted to a control computer; the control computer sets the coordinate data of the red laser light as $X_1$, $Y_1$, $Z_1$, meaning target coordinate data of the three-dimensional verification phantom is converted into left-and-right movement data $X_1'$ and forward-and-backward movement data $Y_1'$ of the moving platform, and height data $Z_1'$ of the lifting platform; then, the moving platform and the lifting platform are controlled to reach a predetermined target position $X_1'$, $Y_1'$, $Z_1'$; at this time, the positioning mark line of the three-dimensional verification phantom corresponds to a corresponding position $X_1$, $Y_1$, $Z_1$ of the red laser light; with implementation of a verification plan, the treatment bed continuously moves forward; when high-energy rays irradiate a circuit part, meaning the ionization chamber part is irradiated by the rays, and the ionization chamber monitors ray irradiation reaching a threshold, the control computer immediately issues an early warning to remind a physicist; if beam emission of the rays does not stop, and a cumulative dose monitored by the ionization chamber reaches a second threshold, the moving platform is automatically driven to move in a direction of bed withdrawal and exit the treatment aperture of the TOMO.

2. The automatic positioning device for helical tomotherapy plan verification according to claim 1, wherein the lifting platform is a scissor lifting platform, and a plurality of metal sleeves are arranged outside the lifting platform, and the plurality of metal sleeves are sleeved layer by layer.

3. The automatic positioning device for helical tomotherapy plan verification according to claim 1, wherein the moving platform is a biaxial moving platform.

4. The automatic positioning device for helical tomotherapy plan verification according to claim 1, wherein the sleeve is an equivalent water material sleeve.

5. The automatic positioning device for helical tomotherapy plan verification according to claim 1, wherein a counterweight is fixedly connected to an end, away from the treatment aperture, of the bearing platform.

6. The automatic positioning device for helical tomotherapy plan verification according to claim 1, wherein each of four corners of a bottom of the base is provided with a through hole, and a support nut is threadedly connected in the through hole.

7. The automatic positioning device for helical tomotherapy plan verification according to claim 1, wherein the sleeve is threadedly connected to positioning bolts, and ends of the positioning bolts penetrate through the sleeve to contact with the support rod.

* * * * *